United States Patent
Truschel et al.

(10) Patent No.: US 10,814,081 B2
(45) Date of Patent: Oct. 27, 2020

(54) DETECTING A MALFUNCTION DURING SPONTANEOUS MECHANICAL VENTILATION

(71) Applicant: KONINKLIJKE PHILIPS N.V., Eindhoven (NL)

(72) Inventors: William Anthony Truschel, Oakmont, PA (US); John Seymour, New Kensington, PA (US)

(73) Assignee: Koninklijke Philips N.V., Eindhoven (NL)

( * ) Notice: Subject to any disclaimer, the term of this patent is extended or adjusted under 35 U.S.C. 154(b) by 426 days.

(21) Appl. No.: 15/754,651

(22) PCT Filed: Aug. 26, 2016

(86) PCT No.: PCT/IB2016/055107
§ 371 (c)(1),
(2) Date: Feb. 23, 2018

(87) PCT Pub. No.: WO2017/033157
PCT Pub. Date: Mar. 2, 2017

(65) Prior Publication Data
US 2018/0264214 A1     Sep. 20, 2018

Related U.S. Application Data

(60) Provisional application No. 62/210,589, filed on Aug. 27, 2015.

(51) Int. Cl.
*A61M 16/00* (2006.01)
*A61B 5/08* (2006.01)
*A61B 5/087* (2006.01)

(52) U.S. Cl.
CPC ......... *A61M 16/0051* (2013.01); *A61B 5/087* (2013.01); *A61B 5/0826* (2013.01);
(Continued)

(58) Field of Classification Search
CPC .... A61M 16/0051; A61M 16/021–026; A61M 16/0057–0081;
(Continued)

(56) References Cited

U.S. PATENT DOCUMENTS 5,485,850 A * 1/1996 Dietz ................... A61B 6/541
128/204.23
6,668,824 B1    12/2003 Isaza
(Continued)

FOREIGN PATENT DOCUMENTS

EP    0651971 A1    5/1995
WO    WO2014030098 A1    2/2014

*Primary Examiner* — Kendra D Carter
*Assistant Examiner* — Elliot S Ruddie
(74) *Attorney, Agent, or Firm* — Daniel H. Brean (57) ABSTRACT

The present disclosure pertains to a method and system configured for detecting a gas delivery malfunction in a spontaneous mechanical ventilation mode. In some embodiments, the system comprises a pressure generator, a subject interface, one or more sensors, one or more processors, electronic storage, a user interface, and/or other components. The detection of a gas delivery malfunction in a spontaneous mechanical ventilation mode is implemented by generating a test flow of gas for delivery to an airway of a subject, and monitoring a responsive flow of gas in the subject interface. If one or more parameters associated with the responsive flow of gas demonstrate inconsistencies with a reference flow of gas responsive to the test flow under a condition that there is no gas delivery malfunction, the system determines that there is a gas delivery malfunction.

15 Claims, 6 Drawing Sheets

(52) U.S. Cl.
CPC ...... *A61M 16/0057* (2013.01); *A61M 16/024* (2017.08); *A61M 2016/0027* (2013.01); *A61M 2016/0036* (2013.01); *A61M 2016/0039* (2013.01); *A61M 2205/15* (2013.01); *A61M 2205/18* (2013.01); *A61M 2205/3334* (2013.01); *A61M 2205/3553* (2013.01); *A61M 2205/702* (2013.01); *A61M 2230/40* (2013.01)

(58) Field of Classification Search
CPC . A61M 2016/0027–0042; A61M 2205/14–18; A61M 2205/3331–3344; A61M 2205/3553; A61M 2205/70–707; A61M 2230/40–42; A61M 2230/46
USPC .................................................. 600/529–543
See application file for complete search history.

(56) References Cited

U.S. PATENT DOCUMENTS

| | | | |
|---|---|---|---|
| 6,874,502 B1* | 4/2005 | Nashed | A61M 16/04 |
| | | | 128/205.23 |
| 2006/0086357 A1* | 4/2006 | Soliman | A61M 16/0833 |
| | | | 128/204.22 |
| 2007/0185406 A1 | 8/2007 | Goldman | |
| 2007/0227539 A1 | 10/2007 | Schwaibold | |
| 2010/0147303 A1* | 6/2010 | Jafari | A61M 16/026 |
| | | | 128/204.23 |
| 2011/0313689 A1 | 12/2011 | Holley | |
| 2012/0272962 A1* | 11/2012 | Doyle | A61M 16/0051 |
| | | | 128/204.23 |
| 2017/0100554 A1* | 4/2017 | Adametz | A61M 16/026 |
| 2018/0015244 A1* | 1/2018 | Isaza | A61M 16/0833 |

* cited by examiner

DETECTING A MALFUNCTION DURING SPONTANEOUS MECHANICAL VENTILATION

CROSS-REFERENCE TO RELATED APPLICATIONS

This patent application claims the priority benefit under 35 U.S.C. § 371 of international patent application no PCT/IB2016/055107, filed Aug. 26, 2016, which claims the priority benefit under 35 U.S.C. § 119(e) of U.S. Provisional Application No. 62/210,589 filed on Aug. 27, 2015, the contents of which are herein incorporated by reference.

BACKGROUND OF THE INVENTION

1. Field of the Invention

The present disclosure pertains to a method and system for detecting a gas delivery malfunction during spontaneous mechanical ventilations modes.

2. Description of the Related Art

Clinicians providing mechanical ventilation assistance to patients rely on a variety of alarms to alert them to unsafe patient conditions or to unsafe conditions with the ventilation equipment itself. Many of these alarms, such as low respiratory rate, low tidal volume, low inspiratory pressure, and circuit disconnect, rely on the delivery of a gas to determine if an alarm state exists. There are some situations where patients are provided mechanical assistance without utilizing a backup rate, such as spontaneous (S) mode continuous positive airway pressure (CPAP) ventilation, or assisted control ventilation (AC) without a rate. These situations decrease the sensitivity of alarms, for example, the circuit disconnection alarm. For example, in spontaneous modes of ventilation, no breath may occur after mucous has plugged the patient interface such as a tracheostomy tube, and therefore, the detection of a circuit disconnection is indistinguishable from an apnea. There is a need to provide an improved solution to detect a gas delivery malfunction during spontaneous mechanical ventilation modes.

SUMMARY OF THE INVENTION

Accordingly, one or more aspects of the present disclosure relate to a system configured for detecting a gas delivery malfunction in a spontaneous mechanical ventilation mode. The system comprises a pressure generator, a subject interface, one or more sensors, and one or more hardware processors. The pressure generator is configured to generate a first flow of gas for delivery to an airway of a subject, the first flow of gas having a first pulse. The subject interface is configured to place the pressure generator in fluid communication with the airway of the subject. The one or more sensors are operatively coupled to the subject interface and configured to generate one or more output signals related to one or more parameters associated with a second flow of gas in the subject interface, the second flow of gas being responsive to the first flow of gas. The one or more hardware processors are operatively connected to the one or more sensors to receive the output signals and configured by machine-readable instructions to analyze the one or more parameters associated with the second flow of gas; and determine whether there is a gas delivery malfunction based on the analysis.

Yet another aspect of the present disclosure relates to a method for detecting a gas delivery malfunction in a spontaneous mechanical ventilation mode in a system. The system comprises a pressure generator, a subject interface, one or more sensors, and one or more processors. The processor comprises a control component, a test analysis component, an alarm component and a parameter component. The method comprises generating a first flow of gas for delivery to an airway of a subject with the pressure generator, the first flow of gas having a first pulse; communicating the first flow of gas to the airway of the subject with the subject interface; generating output signals related to one or more parameters associated with a second flow of gas in the subject interface with the one or more sensors, the second flow of gas being responsive to the first flow of gas; receiving the output signals with the one or more hardware processors; executing machine-readable instructions with the one or more hardware processors, wherein the machine-readable instructions comprise analyzing the one or more parameters associated with the second flow of gas; and determining whether there is a gas delivery malfunction based on the analysis.

Still another aspect of the present disclosure relates to a system configured for detecting a gas delivery malfunction in a spontaneous mechanical ventilation mode. The system comprises means for generating a first flow of gas for delivery to an airway of a subject, the first flow of gas having a first pulse; means for communicating the first flow of gas to the airway of the subject with the subject interface; means for output signals related to one or more parameters associated with a second flow of gas in the subject interface with the one or more sensors, the second flow of gas being responsive to the first flow of gas; and means for receiving the output signals and executing machine-readable instructions with one or more hardware processors, wherein the machine-readable instructions comprise analyzing the one or more parameters associated with the second flow of gas; and determining whether there is a gas delivery malfunction based on the analysis.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
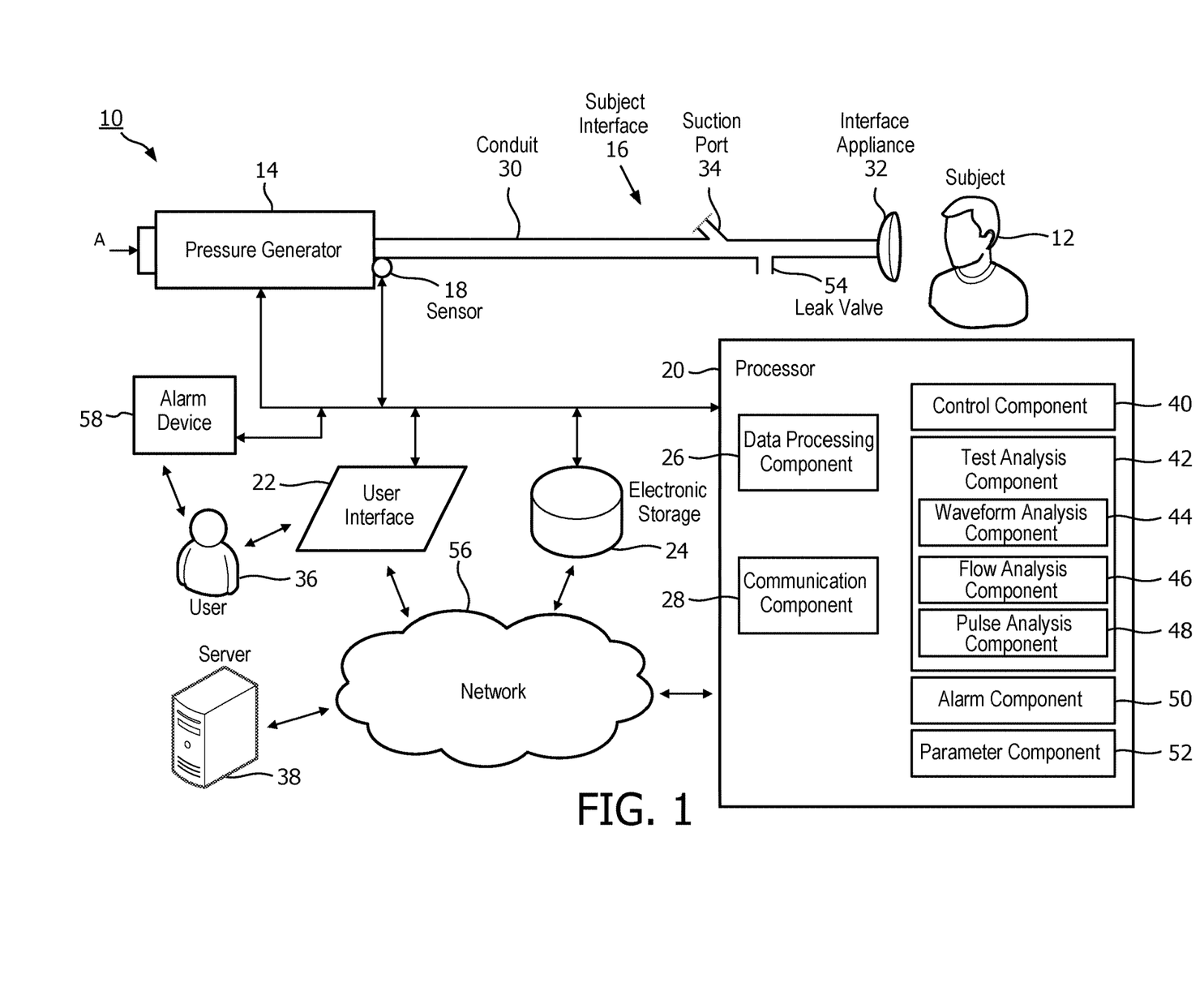
FIG. 1 illustrates an exemplary embodiment of a system configured to detect a subject interface malfunction in a spontaneous mechanical ventilation mode.

FIG. 1 illustrates an exemplary embodiment of a system configured to detect a subject interface malfunction in a spontaneous mechanical ventilation mode. In some embodiments, system 10 comprises a pressure generator 14, a subject interface 16, one or more sensors 18, one or more processors 20, a user interface 22, an alarm device 58, one or more electronic storages 24, and/or other components. System 10 is configured to produce a test pressure in subject interface 16 for delivery to the airway of subject 12 after an alarm interval during which no breath is observed from subject 12, and monitor a subsequent flow of gas in subject interface 16. The subsequent flow of gas is a responsive flow of gas to the test pressure delivered to subject interface 16. The test pressure is a pressurized flow of gas having a test pulse that lasts for approximately 0.5 second. When there is no gas delivery malfunction, the test pressure is delivered to the airway of the subject, and lungs of subject 12 are stretched by inhaling of the test flow of gas. As the test pressure ceases, the subject's lungs rebound and exhale the air, thus generating a responsive flow of gas.

In some embodiments when there is a gas delivery malfunction, the responsive flow of gas may partially comprise of exhaled air flow from the subject or comprise of no exhalation from the subject. Under such circumstances, the responsive flow of gas may comprise of a plurality of air flows that are delivered, reflected, scattered, and/or diffused from other sources. System 10 is further configured to analyze one or more characteristics of the responsive flow of gas, and determine whether there is a gas delivery malfunction, and/or what type of gas delivery malfunctions, for example, subject interface 16 disconnected from subject 12, subject interface 16 obstructed by unknown substances, subject interface 16 leaking gas at unknown one or more places, etc. In one embodiment, upon detecting there is a gas delivery malfunction, system 10 automatically generates an alert signal to facilitate medical professionals to check the status of a ventilator and expedite emergency actions if necessary.

Pressure generator 14 is configured to generate a test pressure for delivery to the airway of subject 12 through subject interface 16. In some embodiments, the test pressure is generated without intervening a therapeutic cycle. For example, a CPAP therapeutic pulse lasts for approximate 1 second with a peak pressure level of 10 $cmH_2O$. After the therapeutic pulse ceases, system 10 waits for a predetermined time, i.e., an alarm interval, to determine whether the subject is responsive to the therapeutic pulse. In some embodiments, the alarm interval is set as 5 seconds. If no breath occurred during the alarm interval, the test pressure is generated to perform a quick diagnosis on whether there is a gas delivery malfunction. In some embodiments, the test pressure is automatically delivered to the airway of subject 12 via subject interface 16 to perform a quick diagnosis on whether there exists a gas delivery malfunction, e.g., disconnected, leaking, or occluded, etc., before an alarm signal is generated. The amplitude of the test pressure is configured to be at a non-therapeutic pressure level such that the test pressure does not disturb subject 12.

Figure 2A:
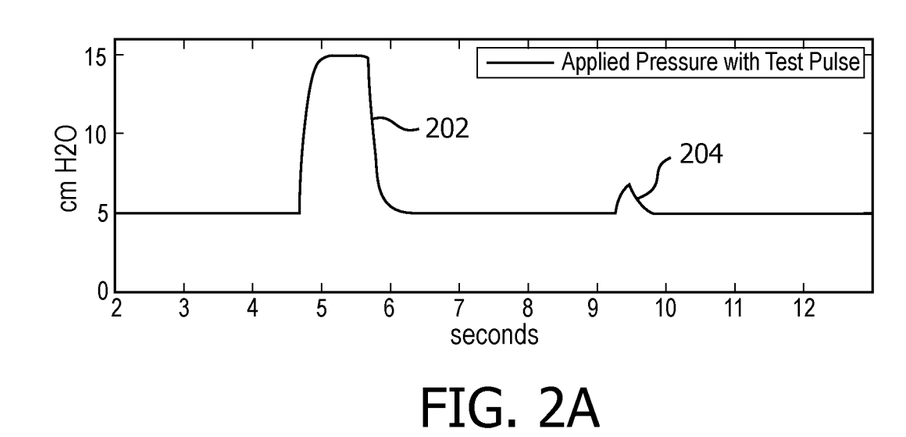
FIG. 2A illustrates an exemplary test pressure having a test pulse generated after a therapeutic pressure waveform.

FIG. 2A illustrates an exemplary test pressure pulse 204 generated after a therapeutic pressure pulse 202. A therapeutic pressure pulse 202 is maintained for approximate 1.5 seconds at a pressure level of 10 $cmH_2O$. After 5 seconds, i.e., a predetermined alarm interval, a test pressure pulse 204 is generated at a pressure level of approximate 2-3 $cmH_2O$. Test pressure pulse 204 as illustrated has an amplitude approximately 5 times less than the amplitude of therapeutic pressure pulse 202, however, the present disclosure is not intended to be limiting. In some embodiments, test pressure pulse 204 may be configured to be at least 4 times less than the therapeutic pressure pulse 202. In some embodiments, test pressure pulse 204 is configured to be 10 times less than therapeutic pressure pulse 202. It should be appreciated that test pressure pulse 204 may be configured to be at a reasonable pressure level that can perform the quick test while not disturbing subject 12 and the therapy that subject 12 is receiving. Therapeutic pressure pulse 202 and test pressure pulse 204 as illustrated are positive pressure pulses applied in a CPAP ventilation therapy, however, the present disclosure is not intended to be limiting. It should be appreciated that therapeutic pressure pulse 202 may be other pressure waveforms that are used for different therapeutic purposes, for example, a positive end expiratory pressure (PEEP) in a PEEP therapy, etc. It should be appreciated that test pressure pulse 204 may be configured in accordance with different therapeutic pressure pulse with respect to different therapeutic purposes.

Returning to FIG. 1, pressure generator 14 receives a gas flow from a gas source, such as but not limited to the ambient atmosphere (indicated by an arrow A in FIG. 1) and elevates the pressure of the received gas flow to a therapeutic pressure level for delivery to the airway of subject 12. At the end of a therapy cycle, pressure generator 14 decreases the therapeutic pressure level to a baseline level and maintains the baseline level for at least a predetermined time to monitor whether there is an alarm situation. In some embodiments, the alarm situation may include low respiratory rate, low tidal volume, low inspiratory pressure, subject interface disconnection, subject interface obstructions, etc. In some embodiments, if no breath from subject 12 is observed within the predetermined time, pressure generator 14 elevates the pressure of the received gas flow to a non-therapeutic pressure level, i.e., generating a test pressure pulse for delivery to the airway of subject 12.

Pressure generator 14 may take the form of any device that is capable of elevating the pressure of the received gas flow for delivery to the airway of subject 12, for example, a pump, blower, piston, or bellows. In some embodiments, pressure generator 14 is a ventilator and/or positive airway pressure device configured to provide therapy. Pressure generator 14 may be configured such that one or more parameters associated with the test flow of gas in addition to and/or other than pressure are adjustable. The one or more parameters may include, for example, one or more of volume, flow rate, temperature, gas composition, velocity, acceleration, and/or other parameters.

Subject interface 16 is configured to interface with the airway of subject 12 and provide fluid communication between pressure generator 14 and the airway of subject 12. In some embodiments, subject interface 16 comprises a conduit 30, an interface appliance 32, and/or other components. Conduit 30 is configured to form a transmission path for the flow of gas to be delivered to interface appliance 32. Conduit 30 may be a flexible length of hose, or other conduit that places interface appliance 32 in fluid communication with pressure generator 14. Interface appliance 32 is configured to deliver the received gas to the airway of subject 12. Interface appliance 32 may be removably coupled to conduit 30 and/or other conduits and/or other interface appliances used to deliver respiratory therapy to subject 12. In some embodiments, interface appliance 32 is non-invasively engaged with subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Examples of non-invasive interface appliance 32 may include a blow tube, a nasal cannula, a nasal mask, a nasal/oral mask, a full face mask, a total face mask, or other interface appliances. In some embodiments, interface appliance 32 is invasive. In some embodiments, interface appliance 32 is invasively engaged with subject 12. Examples of invasive interface appliance 32 may include endotracheal tubes, tracheostomy tubes, and/or other devices.

Subject interface 16 illustrated in FIG. 1 is a single-limbed interface for the delivery of the pressurized flow of gas to the airway of subject 12, however, the present disclosure is not intended to be limiting. The scope of the present disclosure comprises a multi-limbed configuration. The multi-limbed configuration may comprise one inhale limb configured to provide the pressurized flow of gas to the airway of the subject, one exhale limb configured to exhaust gas from the subject, and one leak limb configured to exhaust excess gas from the subject. The multi-limbed configuration may comprise one or more connectors to connect the multiple limbs with subject interface 16, for example, a suction port 34 to connect the inhale limb with conduit 30, and a leak valve 54 to connect the leak limb with conduit 30. The description of the configurations of subject interface 16 is for illustrative purposes only, and is not intended to be limiting. It should be appreciated that subject interface 16 may be implemented as any adjustable configuration based on the requirement of ventilation therapy. As it can be easily pictured that mucous plugged in a tracheostomy tube, an example of invasive interface, causes obstruction in subject interface 16, however, the present disclosure is not intended to be limiting. Obstruction may occur in any type of subject interface including those using non-invasive interface appliances, and may occur in any place of the subject interface.

In some embodiments, circuit disconnection may occur in any place of the subject interface. Examples of disconnections may include disconnection between subject 12 and interface appliance 32, disconnection between conduit 30 and interface appliance 32, disconnection between conduit 30 and suction port 34, disconnection between conduit 30 and leak valve 54, disconnection between conduit 30 and pressure generator 14, other type of disconnections due to unexpected and/or unknown damages, and/or any combinations of the above described connections. The examples of malfunctions set forth above are for illustrative purposes only, and are not intended to be limiting. The present disclosure may include any other types of malfunctions that may lead to an alarm situation in a ventilation therapy.

A sensor or sensors 18 are configured to generate output signals related to the responsive flow of gas to the test pressure in subject interface 16. Sensors 18 are operatively coupled to subject interface 16 to collect data related to one or more parameters related to the real-time measurements associated with the responsive flow of gas. The one or more parameters may comprise flow rate, pressure, volume, temperature, humidity, velocity, and/or other gas parameters. Sensors 18 may be an integrated sensing function unit that is capable to collect all aspect of data measurements. Sensors 18 may comprise one or more sensors, each of which performs a sensing function directed to a specified parameter. The embodiment of FIG. 1 illustrates sensors 18 at a single location within (or in communication with) conduit 30 near pressure generator 14. However, the present disclosure is not intended to be limiting. Sensors 18 may include sensors disposed in different and/or a plurality of locations, such as for example, within or in communication with pressure generator 14, within conduit 30, and/or within interface appliance. Sensors 18 may be configured with wireless communication capabilities to transmit the output signals.

Processor 20 is configured to receive the output signals from sensors 18 and process the real-time measurements related to the one or more parameters read from the output signals. Processor 20 may include one or more of a digital processor(s), analog processor(s), a digital circuit designed to process information, an analog circuit designed to process information, a state machine, a transmitter, a receiver, and/or other mechanism(s) or processor(s) for electronically processing information. Although processor 20 is shown in FIG. 1 as a single entity, this is for illustrative purposes only. In some embodiments, processor 20 may include one or more processing units. The one or more processing units may be physically located within a same device, or processor 20 may represent processing functionality of a plurality of devices operating in coordination. Processor 20 may be configured to execute one or more computer program components. The one or more computer program components comprise a control component 40, a test analysis component 42, an alarm component 50, a parameter component 52, a data processing component 26, a communication component 28, and/or other components. The test analysis component 42 may further comprise a waveform analysis component 44, a flow analysis component 46, and a pulse analysis component 48. Processor 20 may be configured to execute components 26, 28, 40, 42, 44, 46, 48, 50 and 52 by software; hardware; firmware; some combination of software, hardware, and/or firmware; and/or other mechanisms for configuring processing capabilities on processor 20.

Each of the one or more computer programmed components comprises a set of algorithms implemented on processor 20 that instructs processor 20 to perform one or more functions related to ventilation therapy, gas delivery malfunction detection, and/or other operations. For example, control component 40 comprises algorithms implemented on processor 20 that instruct processor 20 to perform controlling of pressure generator 14 to generate the pressurized flow of gas. Test analysis component 42 comprises algorithms implemented on processor 20 that instruct processor 20 to analyze information related to real-time measurements of the one or more parameters associated with the responsive flow of gas in subject interface 16. Waveform analysis component 44 comprises algorithms implemented on processor 20 that instruct processor 20 to analyze waveform characters of the responsive flow of gas to the test flow in subject interface 16. Flow analysis component 46 comprises algorithms implemented on processor 20 that instruct processor 20 to analyze a flow rate of the responsive flow of gas to the test flow in subject interface 16.

Pulse analysis component 48 comprises algorithms implemented on processor 20 that instruct processor 20 to analyze amplitude of a responsive pulse in the responsive flow of gas in subject interface 16. Alarm component 50 comprises algorithms implemented on processor 20 that instruct processor 20 to generate an alarm signal when it is determined there is a gas delivery malfunction. Parameter component 52 comprises algorithms implemented on processor 20 that instruct processor 20 to provide one or more parameters related to the therapeutic pressure waveform as well as the non-therapeutic pressure waveform to control component 40 such that pressure generator 14 can generate a pressurized flow of gas in accordance with the one or more parameters. Data processing component 26 comprises algorithms implemented on processor 20 that instruct processor 20 to receive output signals from sensors 18 and process data read out from the output signals. Communication component 28 comprises algorithms implemented on processor 20 that instruct processor 20 to perform communications within one or more components of processor 20, and between processor 20 and other components of system 10 and/or other network components.

It should be appreciated that although components 26, 28, 40, 42, 44, 46, 48, 50 and 52 are illustrated in FIG. 1 as being co-located within a single processing unit, in implementations in which processor 20 includes multiple processing units, one or more of these components may be located remotely from the other components. The description of the functionality provided by the different components 26, 28, 40, 42, 44, 46, 48, 50 and 52 described below is for illustrative purposes, and is not intended to be limiting, as any of components 26, 28, 40, 42, 44, 46, 48, 50 and 52 may provide more or less functionality than is described. For example, one or more of components 26, 28, 40, 42, 44, 46, 48, 50 and 52 may be eliminated, and some or all of its functionality may be provided by other ones of components 26, 28, 40, 42, 44, 46, 48, 50 and 52. As another example, processor 20 may be configured to execute one or more additional components that may perform some or all of the functionality attributed below to one of components 26, 28, 40, 42, 44, 46, 48, 50 and 52.

Control component 40 is configured to control pressure generator 14 to generate a pressurized flow of gas for delivery to the airway of subject 12. The flow of gas may be a therapeutic flow of gas for delivery to the airway of subject 12 in accordance with the requirement of therapy. In some embodiments, the pressurized flow of gas may be a non-therapeutic flow of gas for delivery to the airway of subject 12 for the purpose of diagnosis of whether there is a malfunction in gas delivery. Control component 40 may determine one or more initial parameters related to the therapeutic flow of gas, the non-therapeutic flow of gas, and/or other types of flow of gas, and further instruct pressure generator 14 to generate a pressurized flow of gas in accordance with the one or more initial parameters. The one or more initial parameters in various situations and/or for various purposes, may be determined during manufacturing, determined based on real-time input received at user interface 22, determined based on historical information related to one or more previous therapies and/or tests received by subject 12, and/or determined by other methods.

Control component 40 is further configured to dynamically adjust the one or more initial parameter based on an output from alarm component 50 and send an updated instruction to pressure generator 14 to generate the pressurized flow of gas in accordance with the adjusted one or more initial parameters. For example, if the output from alarm component 50 indicates that no breath from subject 12 occurred with the alarm interval, control component 40 instructs pressure generator 14 to generate the flow of gas at the non-therapeutic pressure level defined by a set of non-therapeutic pressure parameters. If the output from alarm component 50 indicates that subject 12 is breathing normally, control component 40 instructs pressure generator 14 to generate the flow of gas at the therapeutic pressure level defined by a set of therapeutic pressure parameters. In some embodiments, control component 42 may control pressure generator 14 to generate the flow of gas at various pressure level in accordance with the requirements of different types of therapy, which comprises but not limited to, CPAP, PEEP, bi-level positive airway pressure support, proportional positive airway pressure support, and/or other types of pressure support therapy.

Test analysis component 42 is configured to analyze information related to real-time measurements of the one or more characteristics associated with the responsive flow of gas to the test pressure in subject interface 16. As such, parameter analysis component 42 may further comprises a waveform analysis component 44, a flow analysis component 46 and a pulse analysis component 48.

Waveform analysis component 44 is configured to analyze waveform characters of the responsive flow of gas to the test pressure in subject interface 16. A normal responsive flow of gas from subject 12 under the condition of no gas delivery malfunctions demonstrates an in phase waveform corresponding to the test pressure and comprises a reactance to the pressure waveform. In the waveform of a normal responsive flow of gas, the reactance is illustrated as a variation in the flow rate out of phase or asynchronous with the pressure pulse. The variation may occur because the elastic properties of the lungs are emptying the small inhaled flow of gas stimulated from the test pulse. However, a reactance may result from a patient's stretch receptors having initiated a muscular response in the diaphragm and a new breath may be instantly initiated. A variation in the flow rate may also be a result of the patient heart pushing a small amount of air in and out of the airway, or from swallowing, from speaking, etc. In some embodiments, a variation in the flow rate may be due to the varying flow of gas when the patient is coughing. In all the examples of variations, if the positive measurement in gas flow variation is asynchronous with the test pressure pulse, we may conclude that there is no malfunction in the gas delivery system. When there is a malfunction in the gas delivery such as a disconnection from the airway of subject 12, or an occlusion in subject interface 16, there will be no change in flow when the change in pressure from the test pulse has ceased changing. In some embodiments, when there is no malfunction, we will observe the elastic recoil indicating a return of the small inhaled gas flow produced by the test pressure pulse to a baseline value. It should be appreciated that the examples of the flow rate variations and/or the elastic recoil are for illustrative purpose, and are not intended to be limiting.

Figure 2B:
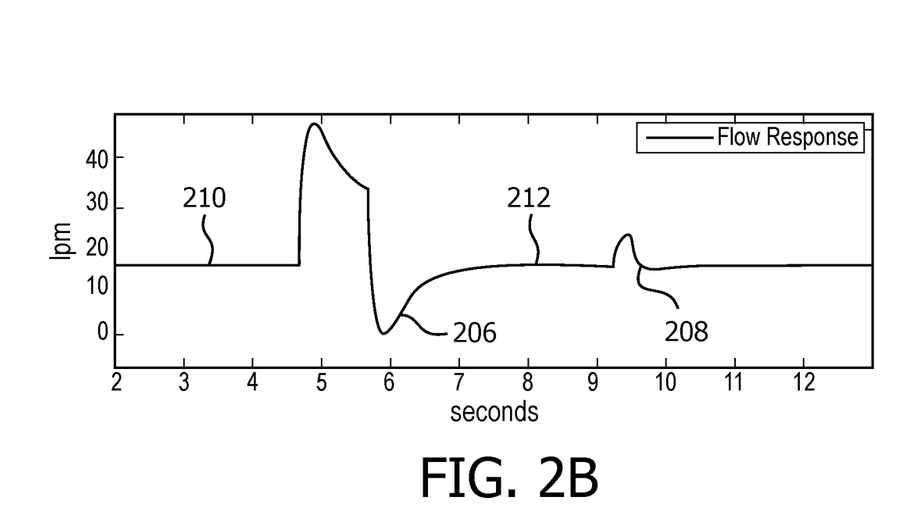
FIG. 2B illustrates an exemplary responsive flow of gas having a responsive pulse under the condition of no gas delivery malfunction.

FIG. 2B illustrates an exemplary responsive flow of gas having a responsive pulse under the condition of no gas delivery malfunction. During a therapeutic cycle started at approximate 4.8 seconds, elastic recoil 206 occurs at the end of the cycle; while during the test cycle started at approximate 9.2 seconds, elastic recoil 208 occurs at the end of the test cycle. Despite that no breath of subject 12 is observed during the predetermined alarm interval, elastic recoil 208 presenting in the test cycle indicates that subject 12 appears breathing normally as the lungs of subject 12 are rebounding as expected. Further, elastic recoil 208 also indicates that there is no gas delivery malfunction.

Returning to FIG. 1, waveform analysis component 44 evaluates whether the waveform of the responsive flow of gas is in phase with the test flow of gas, and whether the waveform comprises elastic recoil or some other variation indicative of a valid connection to subject 12. If the waveform of the responsive flow of gas is out of phase with the test pressure, and the waveform comprises elastic recoil or some other variation, waveform analysis component 44 determines that there is no gas delivery malfunction. On the contrary, if the waveform of the responsive flow of gas is in phase with the test flow of gas, and contains no out of phase variation of any sort; waveform analysis component 44 determines that there is a gas delivery malfunction. The example of malfunctions described above is for illustrative purposes only, however, the present disclosure is not intended to be limiting. It should be appreciated that any discrepancies between a normal responsive flow of gas and an actual observed responsive flow of gas may indicate some types of gas delivery malfunctions.

Flow analysis component 46 is configured to analyze a flow rate of the responsive flow of gas to the test pressure in subject interface 16. In some embodiments, flow analysis component 46 analyzes a baseline flow rate of the responsive flow of gas. Under the condition that there is no gas delivery malfunction, the baseline flow rate of the responsive flow of gas is at the same level of the baseline flow rate of the therapeutic flow of gas. FIG. 2B shows that the baseline flow rate 212 of the responsive flow of gas is at the same level of the baseline flow rate 210 of the therapeutic flow of gas. If the baseline flow rate of the responsive flow of gas is not at the same level of the baseline flow rate of the therapeutic flow of gas, for example, being elevated to a higher baseline level, flow analysis component 46 determines that there is a gas delivery malfunction, and the malfunction is caused by a disconnection between subject 12 and subject interface 16.

Figure 4A:
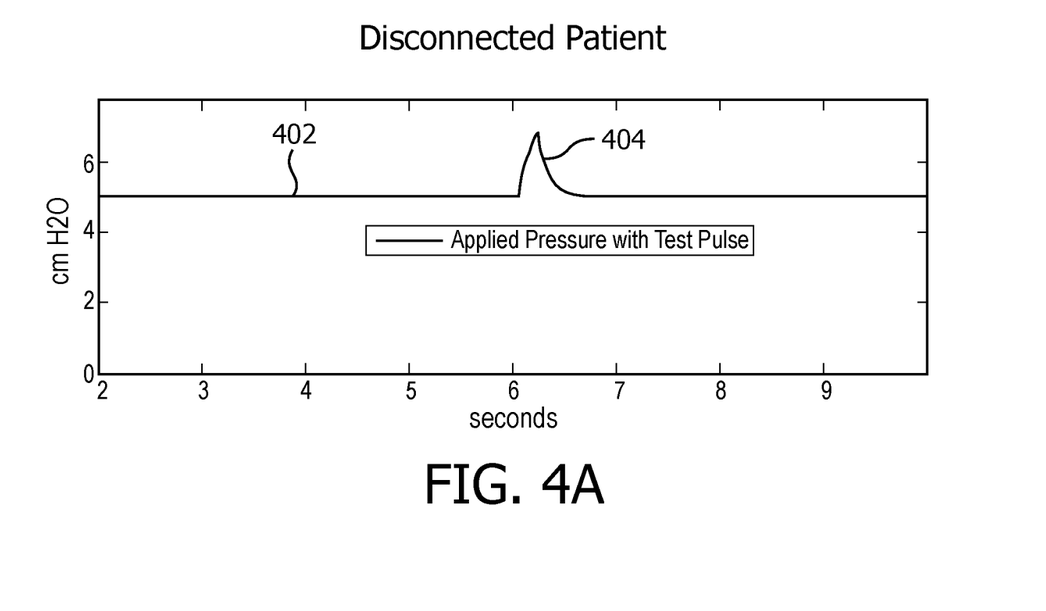
FIG. 4A illustrates an exemplary test pressure having a test pulse generated after a therapeutic pressure waveform.
Figure 4B:
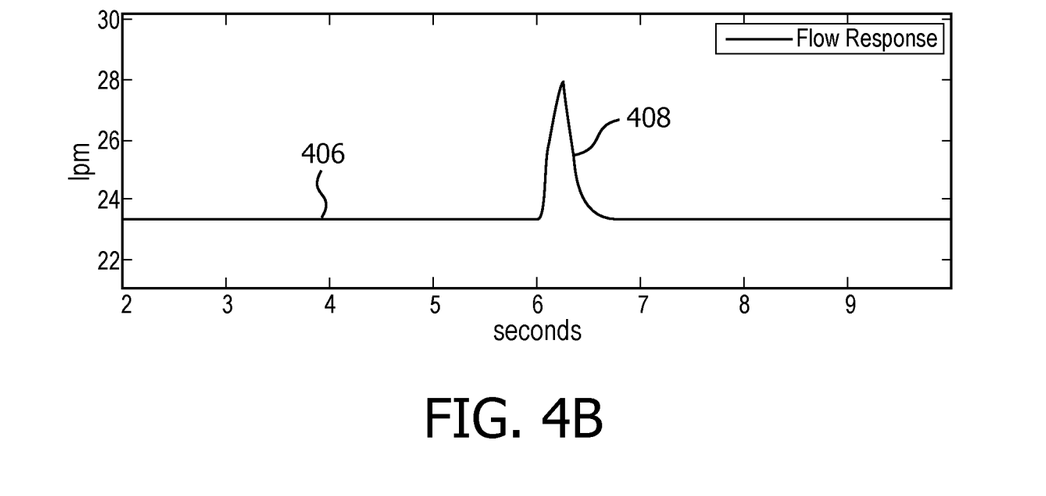
FIG. 4B illustrates an exemplary responsive flow of gas having a responsive pulse under the condition of a gas delivery malfunction caused by a disconnection between the subject and the subject interface.

FIGS. 4A and 4B illustrate an example of a test flow of gas having a test pulse generated after a therapeutic pressure waveform and a responsive flow of gas having a responsive pulse under the condition of a gas delivery malfunction caused by a disconnection between subject 12 and subject interface 16. The therapeutic pressure waveform and the responsive therapeutic flow are not shown; however, the parameters related to the therapeutic pressure waveform and the responsive therapeutic flow are the same as illustrated in FIGS. 2A and 2B. FIG. 4A shows a test flow of gas 402 is delivered to the airway of subject 12 having a test pressure pulse 404 of approximate 2 cmH$_2$O. FIG. 4B shows a responsive flow of gas 406 which comprises a responsive pulse 408 having maximum amplitude of approximate 5 lpm (liter per minute). The baseline flow rate of the responsive flow of gas 406 is approximate 23.5 lpm. Comparing to the baseline flow rate 210 of the therapeutic flow of gas shown in FIG. 2B, the baseline flow rate of the responsive flow of gas 406 is increased for about 7.5 lpm. The increase of the baseline flow rate may be due to one or more other air flows received at the disconnected end of subject interface 16, but can be any types of air flows or turbulences received at the disconnected end. As subject interface 16 is disconnected from subject 12, the responsive flow of gas 406 is an expected reactance of subject interface 16 itself, and thus, demonstrates no elastic recoil or other variation indicative of subject being in a normal condition. The example of malfunction caused by a disconnection described above is for illustrative purposes only, however, the present disclosure is not intended to be limiting. It should be appreciated that any changes of the baseline flow rate level in the responsive flow of gas to the test pressure that is only in phase with the pressure pulse may indicate some types of gas delivery malfunctions. It should further be appreciated that the changes of the baseline flow rate level in the responsive flow of gas may be used alone and/or in combination with other parameters associated with the responsive flow in determining of a malfunction caused by a disconnection between subject 12 and subject interface 16.

Returning to FIG. 1, pulse analysis component 48 is configured to analyze amplitude of a responsive pulse in the responsive flow of gas in subject interface 16. Under the condition that there is no gas delivery malfunction, the responsive flow of gas to the test flow demonstrates a responsive pulse at an expected strength as the lungs of subject 12 rebound normally in exhalation.

Figure 5A:
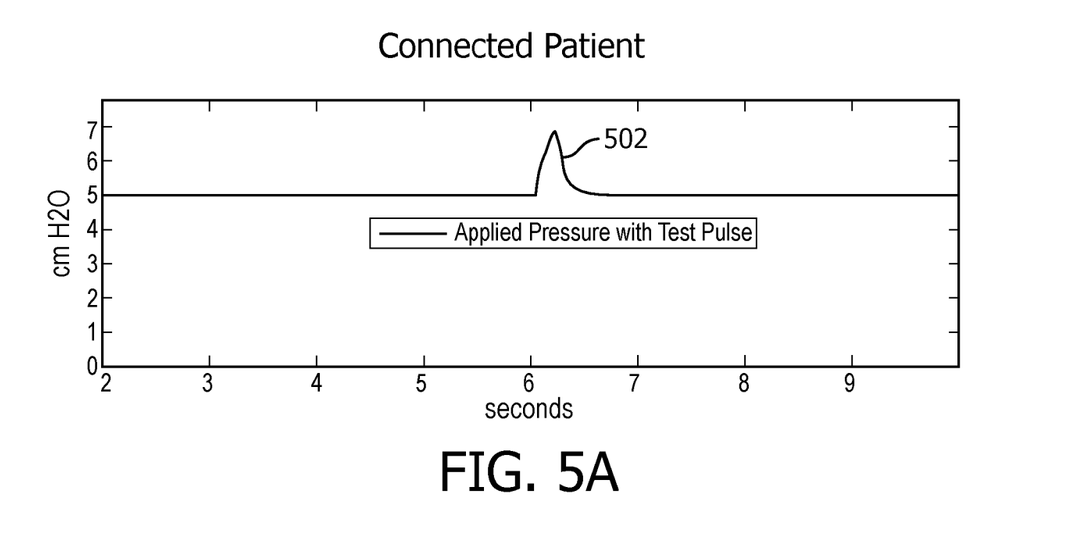
FIG. 5A illustrates another exemplary test pressure having a test pulse generated after a therapeutic pressure waveform.
Figure 5B:
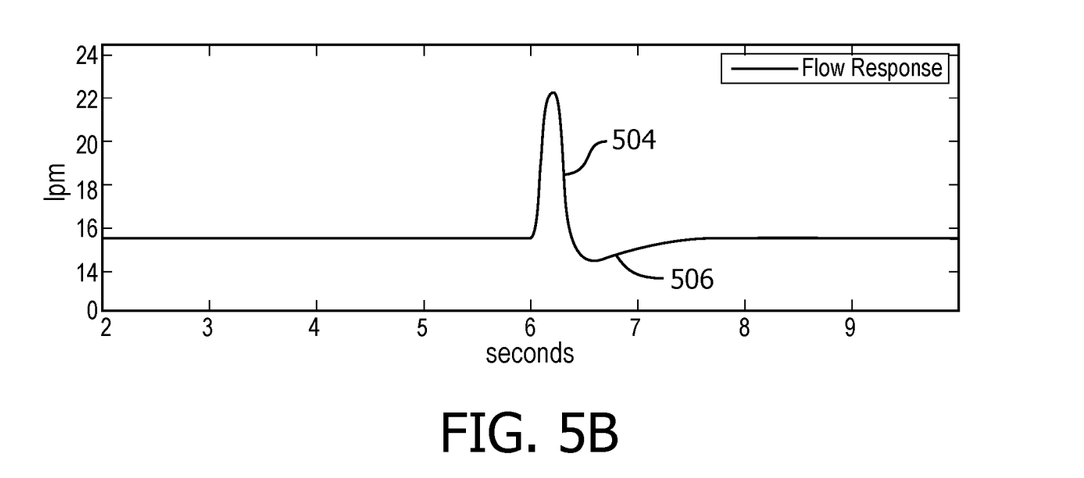
FIG. 5B illustrates an exemplary responsive flow of gas having a responsive pulse under the condition of no gas delivery malfunction.

FIG. 5A illustrates another exemplary test flow of gas having a test pulse generated after a therapeutic pressure waveform, and FIG. 5B illustrates an exemplary responsive flow of gas having a responsive pulse under the condition of no gas delivery malfunction. The therapeutic pressure waveform and the responsive therapeutic flow are not shown; however, the parameters related to the therapeutic pressure waveform and the responsive therapeutic flow are the same as illustrated in FIGS. 2A and 2B. FIG. 5A shows a test flow of gas 502 is delivered to the airway of subject 12 having a test pulse of approximate 2 cmH$_2$O. FIG. 5B shows a responsive flow of gas 504 is observed which comprises a responsive pulse 504 having maximum amplitude of approximate 7.2 lpm, and an elastic recoil 506. However, when there is an obstruction in subject interface 16, the exhalation from the lungs of subject 12 may be partially or completely occluded before the responsive flow of gas reaches sensors 18, and thus, the amplitude of the observed responsive pulse may be very low.

Figure 3A:
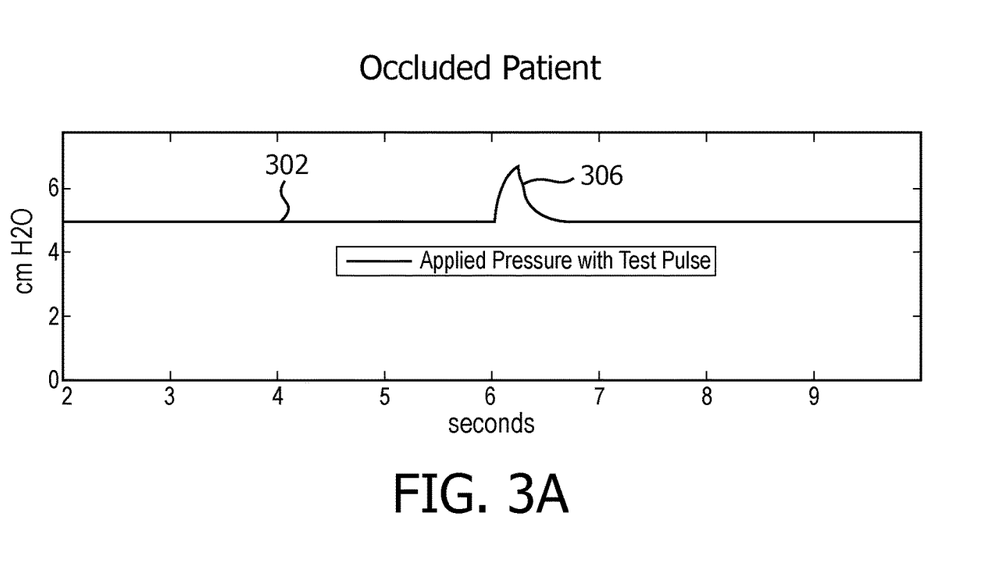
FIG. 3A illustrates an exemplary test pressure having a test pulse generated after a therapeutic pressure waveform.
Figure 3B:
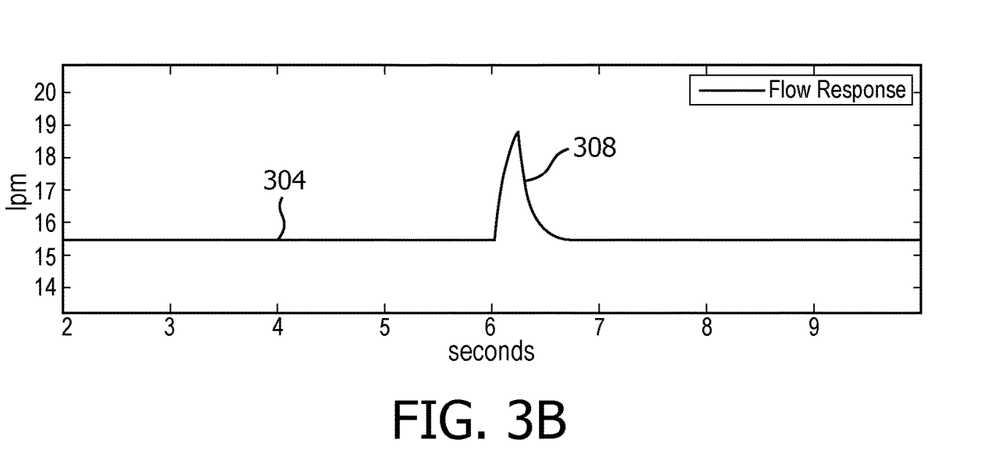
FIG. 3B illustrates an exemplary responsive flow of gas having a responsive pulse under the condition of a gas delivery malfunction caused by an obstruction in the subject interface.

FIG. 3A illustrates an exemplary test pressure having a test pulse after a therapeutic pressure waveform, and FIG. 3B illustrates an exemplary responsive flow of gas having a responsive pulse under the condition of a gas delivery malfunction caused by obstruction in subject interface 16. The therapeutic pressure waveform and the responsive therapeutic flow are not shown; however, the parameters related to the therapeutic pressure waveform and the responsive therapeutic flow are the same as illustrated in FIGS. 2A and 2B. FIG. 3A shows a test pressure 302 is delivered to the airway of subject 12 having a test pulse 306 of approximate 2 $cmH_2O$. FIG. 3B shows a responsive flow of gas 304 which comprises a responsive pulse 308 having maximum amplitude of approximate 3.5 lpm. The maximum amplitude of the responsive pulse 308 in the condition of obstruction is decreased to less than half of the normal responsive pulse 504. Based on the above observation of the responsive flow of gas, pulse analysis component 48 determines that there is a gas delivery malfunction, and the malfunction is caused by an obstruction in subject interface 16.

In some embodiments, the obstruction in subject interface 16 may cause the exhalation flow leaking from leak valve 54. As such, the maximum amplitude of the responsive pulse may be equal to an expected leakage level at a given pressure. Further, as the air flow due to the rebounds of the lungs of subject 12 or another typical biological function is partially or completely obstructed, the responsive flow of gas 304 demonstrates no variation beyond the test pulse. The example of malfunction caused by an obstruction in subject interface 16 described above is for illustrative purposes only, however, the present disclosure is not intended to be limiting. It should be appreciated that any changes of the amplitude of the responsive pulse in the responsive flow of gas to the test pressure may indicate some types of gas delivery malfunctions and/or other components of system 10. It should further be appreciated that the changes of the amplitude of the responsive pulse in the responsive flow of gas may be used alone and/or in combination with other parameters associated with the responsive flow in determining of a malfunction caused by an obstruction in subject interface 16.

Returning to FIG. 1, alarm component 50 is configured to receive one or more analysis results from waveform analysis component 44, flow analysis component 46, and pulse analysis component 48, and generate an alarm signal to be sent to control component 40 if a gas delivery malfunction is determined. In a spontaneous ventilation mode when no test pulse is applied after the predetermined alarm interval, alarm component 50 immediately generates an alarm signal that alerts a caregiver one or more abnormal parameters related to subject 12 and/or system 10. Examples of such alarm signals may include but not limited to subject apnea, low respiratory rate, low tidal volume, circuit disconnect, and/or other types of abnormal indicators. When a test pulse is applied after the predetermined alarm interval during which no breath is observed from subject 12, based on the received one or more analysis results, alarm component 50 may generate alarm signals with respect to different types of malfunctions. For example, alarm component 50 may generate a first alarm signal at a first tune indicating a malfunction caused by a disconnection between subject 12 and subject interface 16, generate a second alarm signal at a second tune indicating a malfunction caused by an obstruction in subject interface 16, and/or generate a third alarm signal at a third tune indicating a malfunction due to unknown reasons.

It should be understood that using different tunes to indicate different types of malfunctions of the subject interface is for illustrative purposes only. Any audio, video, and/or multimedia methods may be implemented to generate various alarm signals. It should be appreciated that the types of alarm signals are not intended to be limiting; instead, other than the gas delivery malfunctions, the alarm signals may convey all kinds of information related to the subject, the on-going therapy, and/or system 10. The diversity of the alarm signals may facilitate the caregivers to act immediately under a medical emergency.

Alarm device 58 is configured to play the alarm signal generated by alarm component 50 in an audio format, and/or display the alarm signal in a combination of formats such as audio, image, animated image, video, text etc. Alarm device 58 may be configured with an audio interface such as a speaker, an image/video/text interface such as a screen to display information related to the alarm signal. For example, alarm device 58 may play a first tune indicating a malfunction caused by a disconnection, and/or with a flash graphic showing an example of disconnection, and/or with a short text message of "Mask disconnected." The above example is for illustrative purpose only, and is not intended to be limiting. Alarm device 58 may play a tune, vibrate, display an image and/or animated image, display a video, display a text description, and/or other operations to alert caregivers. Alarm device 58 is illustrated in FIG. 1 as a separate component from user interface 22; however, the present disclosure is not intended to be limiting. Alarm device 58 may be configured to incorporate the function of user interface 22, and therefore, alarm device 58 and user interface 22 may be integrated as one component.

In some embodiments, alarm device 58 may comprise one or more alarm devices that can be carried wirelessly and are capable of communicating with processor 20 using wireless communication. In some embodiments, the one or more alarm devices may be connected to a network connection port using a communication cable. In some embodiments, the one or more alarm devices may have different functional configurations. For example, a first alarm device is placed in the subject's room and configured to accept user inputs and generate only audio beeps with respect to an alarm signal; a second alarm device is hand-carried by a nurse and configured to generate audio sound with a text description; and a third alarm device is connected to a patient monitoring station using a communication cable and configured to display an image and/or animated image, a video, a text description, and/or an audio sound. It should be appreciated that the above description of alarm device 58 is for illustrative purpose only, and is not intended to be limiting.

Parameter component 52 is configured to provide one or more parameters related to the therapeutic pressure waveform as well as the non-therapeutic pressure waveform to control component 40 such that control component 40 instructs pressure generator 14 to generate a pressurized flow of gas in accordance with the instruction. Parameter component 52 may store an initial set of parameters from manufacturing, an adjusted set of parameters in accordance with user inputs, one or more parameters related to the test analysis, other parameters related to the alarm signal settings, and/or any other parameters related to other components of system 10. In some embodiments, parameter component 52 is configured to provide one or more reference values to test analysis component 42, for example, a reference flow rate indicating a baseline flow rate of the responsive flow of gas under a condition that there is no gas delivery malfunction, a reference amplitude indicating an amplitude of a responsive pulse in the response flow of gas under a condition that there is no gas delivery malfunction, etc. The one or more reference values may be determined based on one or more reference follows of gas responsive to a same test pressure pulse. In some embodiments, the one or more reference values may use historical data related to past tests, and can optionally be adjusted or periodically updated by user 36 (e.g., clinicians or physicians) in accordance with new test requirements, such as PEEP, bi-level, proportional positive airway pressure therapies. It should be appreciated that the one or more reference values may include other characteristic parameters associated with the responsive flow of gas such as volume, temperature, gas composition, velocity, acceleration, and/or other parameters, and are not limited to the examples set forth above.

Data processing component 26 is configured to receive output signals from sensors 18 and process data read out from the output signals so that reliable information is forwarded to test analysis component 42. Data collected from sensors 18 may sometimes comprise one or more types of noise signals from the surrounding environment and/or from other sources that affect the accuracy of information read out from the output signals. For example, an elevation of the baseline flow rate related to the responsive flow of gas due to an added noise signal may cause difficulty to distinguish a malfunction caused by a disconnection and a malfunction caused by obstruction. Data processing component 26 may be configured to filter out the interfering noise signals based on one or more algorithms such that data after filtering provides more accurate readings related to the real-time measurements of the one or more parameters.

Communication component 28 is configured to perform communications within one or more components of processor 20, and between processor 20 and other components of system 10 and/or other network components. In some embodiments, communication component 28 communicates with server 38 remotely connected to network 56 and downloads one or more software packages from electronic storage 24 to modify and/or upgrade the functionalities of one or more components of processor 20. In some embodiments, communication component 28 communicates with electronic storage 24 locally connected to processor 20 or remotely connected to network 56 to retrieve historical information related to past therapies associated with the subject and/or other subjects, and provide the historical information to user 36 to determine and/or adjust one or more parameters related to a therapeutic pressure waveform as well as a non-therapeutic pressure waveform, i.e., the testing pressure waveform. The present disclosure contemplates any techniques for communication including but not limited to hard-wired and wireless communications.

Electronic storage 24 is configured to electronically stores information in an electronic storage media. Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may store software packages, information related to past therapies, information related to a plurality of subjects that receive various therapies, information processed by processor 20, information received via user interface 22, and/or other information that enables system 10 to function properly.

User interface 22 is configured to provide an interface between system 10 and user 36. This enables data, results, and/or instructions and any other communicable items, collectively referred to as "information," to be communicated between user 36 and subject interface 16, processor 20, and/or other components of system 10. For example, user 36 may input one or more parameters related to the testing flow of gas including but not limited to the pressure level and duration of the test pulse, which are further transmitted to processor 20 to control pressure generator 14 to generate the testing flow of gas in accordance with the inputted one or more parameters. In some embodiments, information entered through user interface 22 to system 10 may include ventilation therapy initial percussive pressure waveform parameters, frequency range, an oscillating flow rate amplitude effectiveness threshold, and/or other information. Interface devices suitable for inclusion in user interface 22 include a keypad, buttons, switches, a keyboard, knobs, levers, a display screen, a touch screen, speakers, a microphone, a printer, and/or other interface devices. In some embodiments, user interface 22 may include a plurality of separate interfaces. In some embodiments, user 36 may include subject 12, a clinician, a nurse, any caregiver, an interested party, and/or any other entities.

Network 56 is configured to transmit information among a plurality of network components. For example, network 56 receives inputs from user 36 at user interface 22 related to one or more parameters associated with the therapeutic flow of gas for the purpose of therapy, and one or more parameters associated with the non-therapeutic flow of gas for the purpose of testing, and transmits these inputs to processor 20 for further processing. In some embodiments, a request inputted via user interface 22 is received at server 38 via network 56 to retrieve historical information related to past therapies on the subject and/or other subjects for analysis. Network 56 forwards an instruction from server 38 to retrieve the requested historical information related to past therapies on a plurality of subjects from electronic storage 24. Network 56 may be a single network or a combination of multiple networks. For example, network 56 may be a local area network (LAN), a wide area network (WAN), a public network, a private network, a proprietary network, a Public Telephone Switched Network (PSTN), the Internet, a wireless communication network, a virtual network, and/or any combination thereof.

Figure 6:
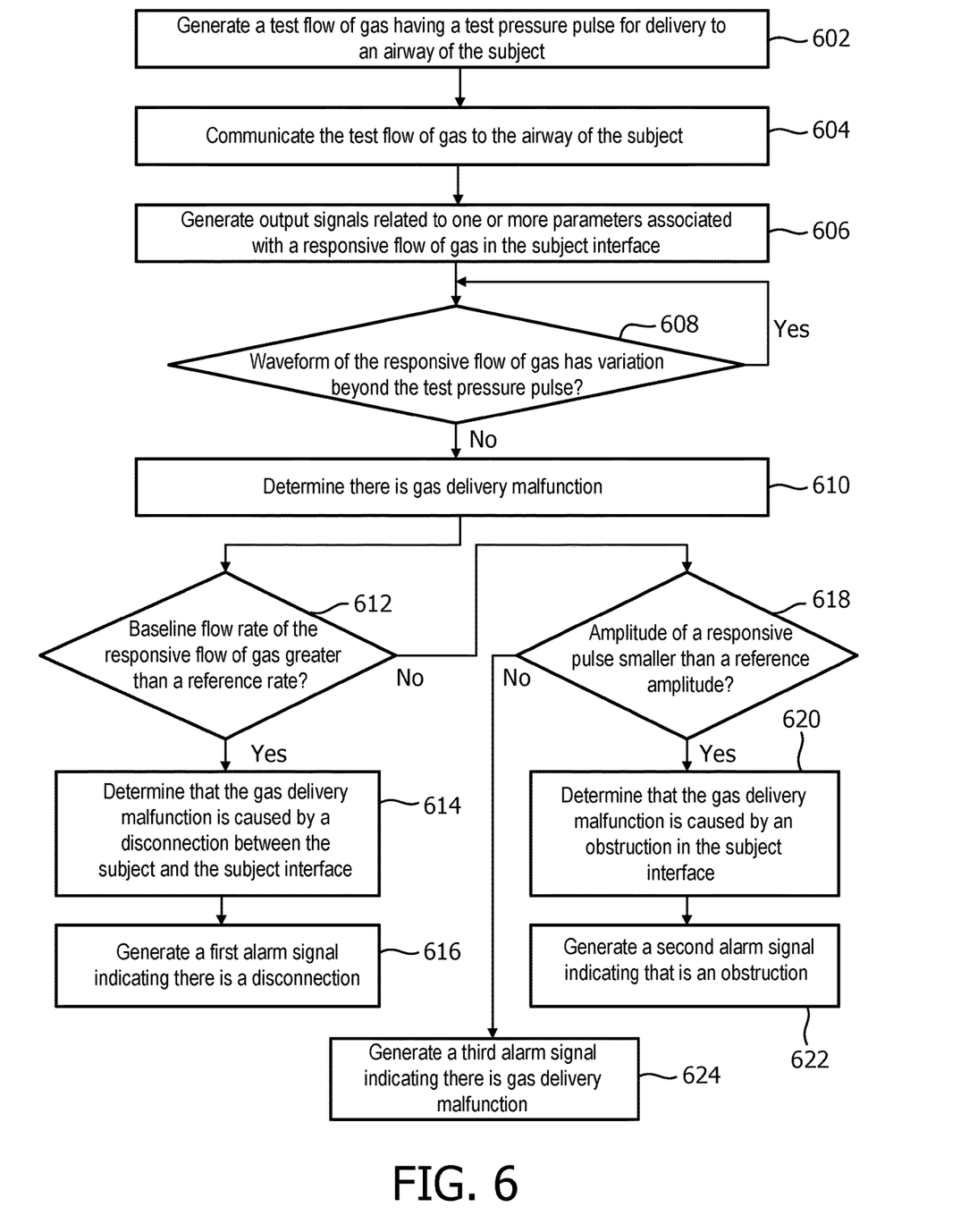
FIG. 6 illustrates an exemplary flowchart of the process for detecting a gas delivery malfunction in a spontaneous mechanical ventilation mode.

FIG. 6 illustrates an exemplary flowchart of the process for detecting a gas delivery malfunction in a spontaneous mechanical ventilation mode. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 6 and described below is not intended to be limiting.

At operation 602, a test flow of gas having a test pressure pulse is generated for delivery to an airway of the subject. In some embodiments, operation 602 is performed by a pressure generator the same as or similar to pressure generator 14 (shown in FIG. 1 and described herein).

At operation 604, the test flow of gas is communicated to the airway of the subject. In some embodiments, operation 604 is performed by a subject interface the same as or similar to subject interface 16 (shown in FIG. 1 and described herein).

At operation 606, output signals related to one or more parameters associated with a responsive flow of gas in the subject interface is generated. In some embodiments, operation 606 is performed by sensors the same as or similar to sensors 18 (shown in FIG. 1 and described herein).

At operation 608, a decision is made as to whether the waveform of the responsive flow of gas in the subject interface has a variation beyond the test pressure pulse. In some embodiments, operation 608 is performed by a waveform analysis component the same as or similar to waveform analysis component 44 (shown in FIG. 1 and described herein).

At operation 610, if the waveform of the responsive flow of gas in the subject interface has no variation beyond the test pressure pulse, it is determined there is a gas delivery malfunction. In some embodiments, operation 610 is performed by a waveform analysis component the same as or similar to waveform analysis component 44 (shown in FIG. 1 and described herein).

At operation 612, a decision is made as to whether the baseline flow rate of the responsive flow of gas is greater than a reference flow rate. In some embodiments, operation 612 is performed by a flow analysis component the same as or similar to flow analysis component 46 (shown in FIG. 1 and described herein).

At operation 614, if the baseline flow rate of the responsive flow of gas is greater than a reference flow rate, it is determined that the gas delivery malfunction is caused by a disconnection between the subject and the subject interface. In some embodiments, operation 614 is performed by a flow analysis component the same as or similar to flow analysis component 46 (shown in FIG. 1 and described herein).

At operation 616, a first alarm signal is generated indicating there is a gas delivery malfunction caused by a disconnection between the subject and the subject interface. In some embodiments, operation 616 is performed by an alarm component the same as or similar to alarm component 50 (shown in FIG. 1 and described herein).

At operation 618, a decision is made as to whether the amplitude of a responsive pulse in the responsive flow of gas is smaller than a reference amplitude. In some embodiments, operation 618 is performed by a pulse analysis component the same as or similar to pulse analysis component 48 (shown in FIG. 1 and described herein).

At operation 620, if the amplitude of a responsive pulse in the responsive flow of gas is smaller than a reference amplitude, it is determined that the gas delivery malfunction is caused by an obstruction in the subject interface. In some embodiments, operation 620 is performed by a pulse analysis component the same as or similar to pulse analysis component 48 (shown in FIG. 1 and described herein).

At operation 622, a second alarm signal is generated indicating there is a gas delivery malfunction caused by an obstruction in the subject interface. In some embodiments, operation 622 is performed by an alarm component the same as or similar to alarm component 50 (shown in FIG. 1 and described herein).

At operation 624, if the baseline flow rate of the responsive flow of gas is not greater than a reference flow rate and the amplitude of a responsive pulse in the responsive flow of gas is not smaller than a reference amplitude, a third alarm signal is generated indicating there is a gas delivery malfunction due to unknown reasons. In some embodiments, operation 624 is performed by a test analysis component the same as or similar to test analysis component 42 (shown in FIG. 1 and described herein), which may include a waveform analysis component the same as or similar to waveform analysis component 44, a flow analysis component the same as or similar to flow analysis component 46, and a pulse analysis component the same as or similar to pulse analysis component 48 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for detecting a gas delivery malfunction in a spontaneous mechanical ventilation mode, the system comprising:

a pressure generator configured to generate a therapeutic flow of gas for delivery to an airway of a subject;

a subject interface configured to place the pressure generator in fluid communication with the airway of the subject;

one or more sensors operatively coupled to the subject interface and configured to generate output signals related to one or more parameters associated with a second flow of gas in the subject interface, the second flow of gas being responsive to the therapeutic flow of gas, the second flow of gas indicative of a breath by the subject; and one or more hardware processors operatively connected to the one or more sensors to receive the output signals and configured by machine-readable instructions to:

analyze the one or more parameters associated with the second flow of gas;

responsive to no breath being detected within a predetermined time interval, cause the pressure generator to generate a test pressure pulse without intervening in a therapeutic cycle, the test pressure pulse being configured to have an amplitude at a non-therapeutic pressure level such that the test pressure pulse does not disturb a therapy being received by the subject;

cause the one or more sensors to generate output signals related to one or more parameters associated with a third flow of gas in the subject interface, the third flow of gas being responsive to the test pressure pulse;

analyze the one or more parameters associated with the third flow of gas; and determine whether there is a gas delivery malfunction based on the analysis of the third flow of gas.

2. The system of claim 1, wherein the amplitude of the test pressure pulse is smaller than an amplitude of the therapeutic flow of gas.

3. The system of claim 1, wherein the one or more hardware processors are further configured to:

analyze a waveform of the third flow of gas;

if the waveform of the third flow of gas has no variation beyond the test pressure pulse, determine that there is a gas delivery malfunction;

analyze a baseline flow rate of the third flow of gas; and if the baseline flow rate of the third flow of gas is greater than a reference flow rate, determine that the gas delivery malfunction is caused by a disconnection between the subject and the subject interface, wherein the reference flow rate is determined based on a reference flow of gas responsive to the therapeutic flow of gas under a condition that there is no gas delivery malfunction.

4. The system of claim 1, wherein the one or more hardware processors are further configured to:

analyze a waveform of the third flow of gas;

if the waveform of the third flow of gas has no variation beyond the test pressure pulse, determine that there is a gas delivery malfunction;

analyze an amplitude of a pulse in the third flow of gas, the pulse being responsive to the test pressure pulse; and if the amplitude of the pulse in the third flow of gas is smaller than a reference amplitude, determine that the gas delivery malfunction is caused by an obstruction in the subject interface, wherein the reference amplitude is determined based on a reference flow of gas responsive to the therapeutic flow of gas under a condition that there is no gas delivery malfunction.

5. The system of claim 1, wherein the one or more hardware processors are further configured to generate an alarm signal indicating there is a gas delivery malfunction.

6. A method for detecting a gas delivery malfunction in a spontaneous mechanical ventilation mode implemented in a system, the system comprising a pressure generator, a subject interface, one or more sensors, and one or more hardware processors, the method comprising:

generating a therapeutic flow of gas for delivery to an airway of a subject with the pressure generator;

communicating the therapeutic flow of gas to the airway of the subject with the subject interface;

generating output signals related to one or more parameters associated with a second flow of gas in the subject interface with the one or more sensors, the second flow of gas being responsive to the therapeutic flow of gas, the second flow of gas indicative of a breath by the subject;

receiving the output signals related to the one or more parameters associated with the second flow of gas with the one or more hardware processors;

executing machine-readable instructions with the one or more hardware processors, wherein the machine-readable instructions comprise:

analyzing the one or more parameters associated with the second flow of gas;

responsive to no breath being detected within a predetermined time interval, causing the pressure generator to generate a test pressure pulse without intervening in a therapeutic cycle, the test pressure pulse being configured to have an amplitude at a non-therapeutic pressure level such that the test pressure pulse does not disturb a therapy being received by the subject;

causing the one or more sensors to generate output signals related to one or more parameters associated with a third flow of gas in the subject interface, the third flow of gas being responsive to the test pressure pulse;

analyzing the one or more parameters associated with the third flow of gas; and determining whether there is a gas delivery malfunction based on the analysis of the third flow of gas.

7. The method of claim 6, wherein the amplitude of the test pressure pulse is smaller than an amplitude of the therapeutic flow of gas.

8. The method of claim 6, wherein the machine-readable instructions further comprise:

analyzing a waveform of the third flow of gas;

if the waveform of the third flow of gas has no variation beyond the test pressure pulse, determining that there is a gas delivery malfunction;

analyzing a baseline flow rate of the third flow of gas; and if the baseline flow rate of the third flow of gas is greater than a reference flow rate, determining that the gas delivery malfunction is caused by a disconnection between the subject and the subject interface, wherein the reference flow rate is determined based on a reference flow of gas responsive to the therapeutic flow of gas under a condition that there is no gas delivery malfunction.

9. The method of claim 6, wherein the machine-readable instructions further comprise:

analyzing a waveform of the third flow of gas;

if the waveform of the third flow of gas has no variation beyond the test pressure pulse, determining that there is a gas delivery malfunction;

analyzing an amplitude of a pulse in the third flow of gas, the pulse in the third flow of gas being responsive to the test pressure pulse; and if the amplitude of the pulse in the third flow of gas is smaller than a reference amplitude, determining that the gas delivery malfunction is caused by an obstruction in the subject interface, wherein the reference amplitude is determined based on a reference flow of gas responsive to the therapeutic flow of gas under a condition that there is no gas delivery malfunction.

10. The method of claim 6, wherein the machine-readable instructions further comprise generating an alarm signal indicating there is a gas delivery malfunction.

11. A system for detecting a gas delivery malfunction in a spontaneous mechanical ventilation mode, the system comprising:

means for generating a therapeutic flow of gas for delivery to an airway of a subject;

means for communicating the therapeutic flow of gas to the airway of the subject;

means for generating output signals related to one or more parameters associated with a second flow of gas in the subject interface, the second flow of gas being responsive to the therapeutic flow of gas, the second flow of gas indicative of a breath by the subject; and means for receiving the output signals and executing machine-readable instructions, wherein the machine-readable instructions comprise:

analyzing the one or more parameters associated with the second flow of gas;

responsive to no breath being detected within a predetermined time interval, causing the means for generating a therapeutic flow of gas to generate a test pressure pulse without intervening in a therapeutic cycle, the test pressure pulse being configured to have an amplitude at a non-therapeutic pressure level such that the test pressure pulse does not disturb a therapy being received by the subject;

causing means for generating output signals to generate output signals related to one or more parameters associated with a third flow of gas in the means for communicating, the third flow of gas being responsive to the test pressure pulse;

analyzing the one or more parameters associated with the third flow of gas, and determining whether there is a gas delivery malfunction based on the analysis of the third flow of gas.

12. The system of claim 11, wherein the amplitude of the test pressure pulse is smaller than an amplitude of the therapeutic flow of gas.

13. The system of claim 11, wherein the machine-readable instructions further comprise:

analyzing a waveform of the third flow of gas;

if the waveform of the third flow of gas has no variation beyond the first test pressure pulse, determining that there is a gas delivery malfunction;

analyzing a baseline flow rate of the third flow of gas; and if the baseline flow rate of the third flow of gas is greater than a reference flow rate, determining that the gas delivery malfunction is caused by a disconnection between the subject and the subject interface, wherein the reference flow rate is determined based on a reference flow of gas responsive to the therapeutic flow of gas under a condition that there is no gas delivery malfunction.

14. The system of claim 11, wherein the machine-readable instructions further comprise:

analyzing a waveform of the third flow of gas;

if the waveform of the third flow of gas has no variation beyond the test pressure pulse, determining that there is a gas delivery malfunction;

analyzing an amplitude of a pulse in the third flow of gas, the pulse in the third flow of gas being responsive to the test pressure pulse; and if the amplitude of the pulse in the third flow of gas is smaller than a reference amplitude, determining that the gas delivery malfunction is caused by an obstruction in the subject interface, wherein the reference amplitude is determined based on a reference flow of gas responsive to the therapeutic flow of gas under a condition that there is no gas delivery malfunction.

15. The system of claim 11, wherein the machine-readable instructions further comprise generating an alarm signal indicating there is a gas delivery malfunction.

* * * * *